(12) United States Patent
Andreasson

(10) Patent No.: US 8,552,059 B2
(45) Date of Patent: Oct. 8, 2013

(54) TREATMENT OF ISCHEMIC EPISODES AND CEREBROPROTECTION THROUGH MISOPROSTOL

(71) Applicant: Katrin Andreasson, Stanford, CA (US)

(72) Inventor: Katrin Andreasson, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/621,977

(22) Filed: Sep. 18, 2012

(65) Prior Publication Data

US 2013/0028883 A1    Jan. 31, 2013

Related U.S. Application Data

(62) Division of application No. 12/763,872, filed on Apr. 20, 2010, now abandoned.

(60) Provisional application No. 61/170,773, filed on Apr. 20, 2009.

(51) Int. Cl.
*A61K 31/215*     (2006.01)
(52) U.S. Cl.
USPC ........................................... 514/530
(58) Field of Classification Search
USPC ............................................ 514/530
See application file for complete search history.

(56) References Cited

U.S. PATENT DOCUMENTS

| 5,985,607 A | 11/1999 | Delcuve et al. |
| 7,547,715 B2 | 6/2009 | Sakai et al. |
| 2006/0201504 A1 * | 9/2006 | Singhal et al. ........... 128/204.18 |

OTHER PUBLICATIONS

Li et al. Misoprostol, an anti-ulcer agent and PGE2 receptor agonist, protects against cerebral ischemia. Neuroscience Letters 438 (2008) pp. 210-215.*
McCullough et al. "Neuroprotective Function of the PGE2 EP2 Receptor in Cerebral Ischemia". J Neurosci, Jan. 2004, 24(1), pp. 257-268.
Oliveira et al. "Modulation of pentylenetetrazol-induced seizures by prostaglandin E2 receptors". Neuroscience, Apr. 2008, 152(4), pp. 1110-1118.
Yuhki et al. The prostaglandin E2-EP4 system protects the heart from ischemia-reperfusion injury. Advances in Heart Diseases, Proceedings of the World Congress on Heart Disease: New Trends in Research, Diagnosis and Treatment, 12th, Vancouver, BC, Canada, Jul. 16-19, 2005 (2006), Meeting date 2005, pp. 337-341.
Ahmad et al. Prostaglandin EP4 receptor agonist protects against acute neurotoxicity. Brain Research, 2005, 1066, pp. 71-77.

* cited by examiner

*Primary Examiner* — Jennifer M Kim
(74) *Attorney, Agent, or Firm* — Andrea Blecken

(57) ABSTRACT

The present invention provides compositions and methods for treating an ischemic episode using misoprostol alone or in combination with anti-thrombotic agents.

9 Claims, 9 Drawing Sheets

TREATMENT OF ISCHEMIC EPISODES AND CEREBROPROTECTION THROUGH MISOPROSTOL

RELATED APPLICATION

Figure 1:
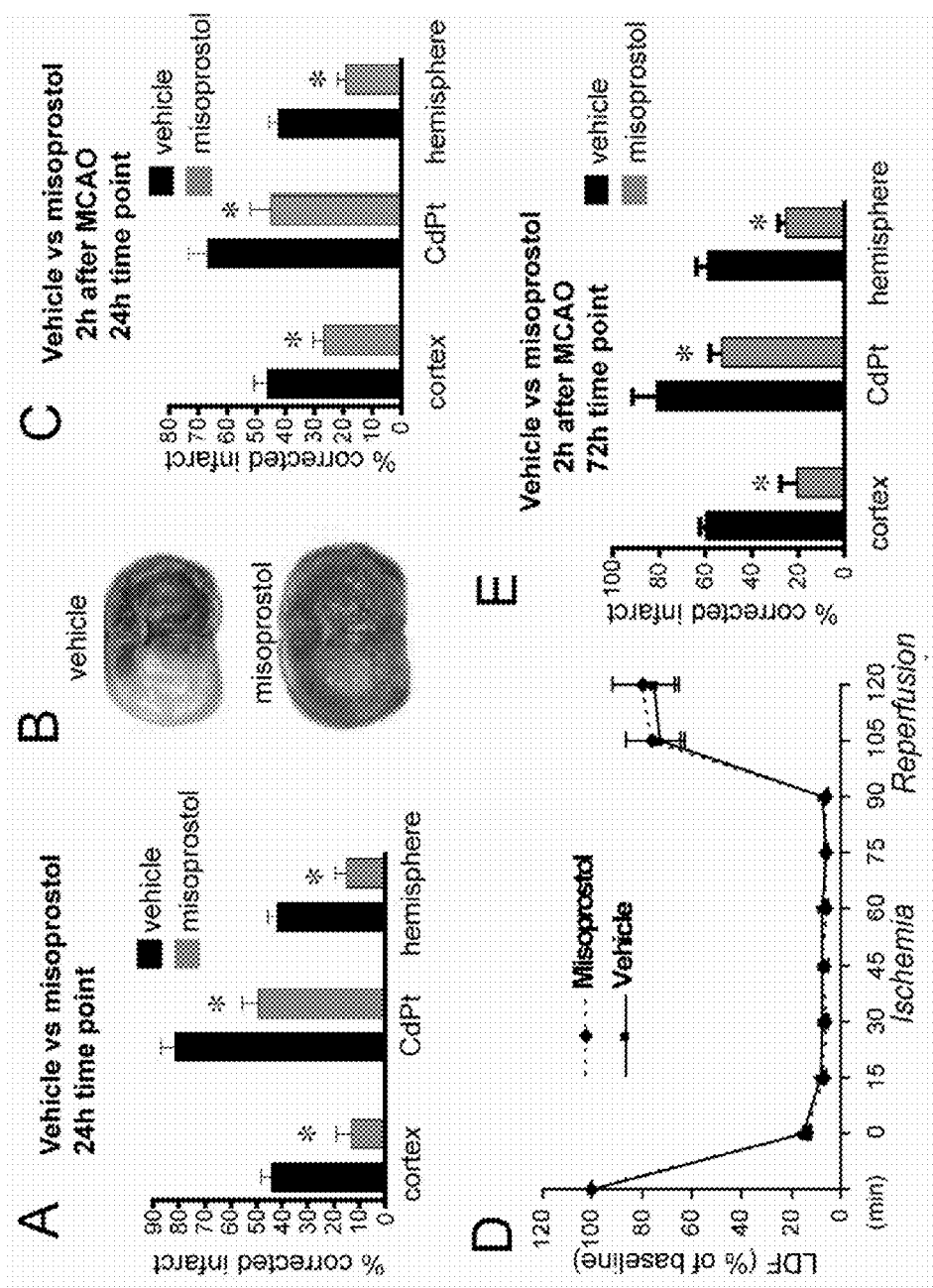

This application is a divisional of U.S. patent application Ser. No. 12/763,872 filed on Apr. 20, 2010, entitled "Treatment of ischemic episodes and neuroprotection through Prostaglandin $E_2$ ($PGE_2$) $EP_2$ and/or $EP_4$ receptor agonists", which claims priority and other benefits from U.S. Provisional Patent Application Ser. No. 61/170,773, filed Apr. 20, 2009, entitled "Treatment of ischemic episodes and neuroprotection through Prostaglandin $E_2$ ($PGE_2$) $EP_2$ and/or $EP_4$ receptor agonists". Its entire content is specifically incorporated herein by reference.

STATEMENT OF GOVERNMENTAL SUPPORT

This invention was made with Government support under contract NS045727 awarded by the National Institutes of Health. The Government has certain rights in this invention.

TECHNICAL FIELD OF THE INVENTION

The present invention relates to the field of cerebroprotection and treatment of episodes of cerebral ischemia.

BACKGROUND

Prostanoids including various prostaglandins (PGs) and thromboxanes (TXs) are cyclooxygenase (COX) metabolites of $C_{20}$-unsaturated fatty acids such as arachidonic acid, whereby the cyclooxygenases COX-1 and COX-2 catalyze the first committed step in the synthesis. Prostanoids exert a variety of actions in various tissues and cells. The most typical actions are the relaxation and contraction of various types of smooth muscles. They also modulate neuronal activity by either inhibiting or stimulating neurotransmitter release, sensitizing sensory fibers to noxious stimuli, or inducing central actions such as fever generation and sleep induction. Prostaglandins also regulate secretion and motility in the gastrointestinal tract as well as transport of ions and water in the kidney. They are involved in apoptosis, cell differentiation, and oncogenesis. Prostanoids also regulate the activity of blood platelets both positively and negatively and are involved in vascular homeostasis and hemostasis (Narumiya et al., 1999). These substances are synthesized in response to various stimuli in a variety of cells, released immediately after synthesis, and act in the vicinity of their synthesis (Smith and Langenbach, 2001).

Among prostanoids, the E type prostaglandins are most widely produced in the body and exhibit the most versatile actions through four different G-protein-coupled receptors designated $EP_1$, $EP_2$, $EP_3$, and $EP_4$, resulting in changes in the production of cAMP and/or phosphoinositol turnover, intracellular $Ca^{2+}$ mobilization and agonist-induced changes in activities of downstream kinases (Coleman et al., 1994; Narumiya et al., 1999).

Stroke is the leading cause of serious, long-term disability and the second leading cause of death in the Western world, ranking after heart disease and before cancer (Donnan et al., 2008). Three million Americans are currently permanently disabled because of ischemic stroke, and 31% of stroke survivors need help caring for themselves, 20% need help walking, 71% have an impaired vocational capacity when examined an average of 7 years later, and 16% have to be institutionalized. Brain injury by transient complete global brain ischemia (cardiac arrest) and regional incomplete brain ischemia (ischemic stroke) afflicts a very large number of patients with death or permanent disability (White et al., 2000).

Cerebral ischemia and reperfusion engage multiple pathways involving loss of membrane integrity that quickly leads to neuronal injury and neuronal death. Free fatty acids, in particular free arachidonic acid, are released during cerebral ischemia as a consequence of the activity of both phospholipase C (activated by depolarization) and phospholipase $A_2$ (activated by increased $Ca^{2+}{}_i$). Early during reperfusion, oxidative metabolism of arachidonate causes a burst of excess oxygen radicals, iron is released from storage proteins by superoxide-mediated reduction, and nitrogen monoxide is generated. Cyclooxygenases catalyze the addition of two molecules of $O_2$ to an unsaturated fatty acid, like arachidonic acid, and produce prostaglandin PGG, which is rapidly peroxidized to prostaglandin PGH with concomitant release of oxygen radicals (White et al., 2000).

A neurotoxic effect of cyclooxygenase-2 (COX-2) has been demonstrated in rodent models of focal cerebral ischemia (Dore et al., 2003; Iadecola et al., 2001; Nagayama et al., 1999; Nogawa et al., 1998). Recent studies examining the mechanisms of COX-2 neurotoxicity have focused on the roles of individual prostaglandin signaling pathways downstream of COX-2. In vivo, the $EP_2$ receptor exerts a significant cerebroprotective effect in both focal and permanent middle cerebral artery occlusion (MCAO) models (Liu et al., 2005; McCullough et al., 2004). Furthermore, the $EP_2$ receptor exerts a cerebroprotective effect against N-methyl D-aspartate (NMDA) excitotoxicity in vivo (Ahmad et al., 2005). Thus, selected prostaglandin signaling systems downstream of COX-2 exert potent beneficial effects in the setting of ischemia.

The treatment of stroke includes preventive therapies using, for example, antihypertensive and anti-platelet drugs, which control and reduce blood pressure and, thus, reduce the likelihood of stroke. The development of anti-thrombotic agents such as tissue plasminogen activator (t-PA), which is currently the only FDA approved therapy for stroke, has provided a significant advancement in the treatment of ischemic stroke patients; however, to be effective, it is necessary to start treatment within a three-hours window after the onset of symptoms.

The development of therapeutic agents and effective methods of treatment for stroke and ischemic episodes in general is of great clinical interest, particularly for cases, where the three-hours window for the effective use of t-PA has been missed.

SUMMARY

Aspects of the present invention provide methods and compositions for the treatment of ischemic episodes, including but not limited to focal or global ischemia of the brain and central nervous system, as caused by stroke or cardiac arrest. Furthermore, the present invention relates to methods and compositions for the treatment or prevention of a neurological disorder that results from the exposure to ischemic episodes, including but not limited to focal or global ischemia of the brain and central nervous system, as caused by stroke or cardiac arrest.

Aspects of the invention include the use of $PGE_2$ $EP_2$ and/or $EP_4$ agonists, alone or in combination with an anti-thrombotic agent such as tissue plasminogen activator, as therapeutic agents for the treatment of ischemic episodes or the prevention of neuronal injury following the exposure to ischemic episodes. The administration of the respective therapeutic agent(s) may be systemic or localized to the brain.

In certain embodiments of the invention, the therapeutic agent is misoprostol alone or in combination with tissue plasminogen activator.

In further embodiments of the invention, the therapeutic agent is ONO-AE1-329 alone or in combination with tissue plasminogen activator.

The invention also provides methods for the identification of compounds that selectively activate the $PGE_2$ $EP_2$ and/or $EP_4$ receptor and that are determined to be efficacious and therapeutically useful in the treatment of ischemic episodes or in the prevention of neuronal injury following the exposure to ischemic episodes.

The above summary is not intended to include all features and aspects of the present invention nor does it imply that the invention must include all features and aspects discussed in this summary.

INCORPORATION BY REFERENCE

All publications and patent applications mentioned in this specification are herein incorporated by reference to the same extent as if each individual publication or patent application was specifically and individually indicated to be incorporated by reference.

DRAWINGS

The accompanying drawings illustrate embodiments of the invention and, together with the description, serve to explain the invention. These drawings are offered by way of illustration and not by way of limitation; it is emphasized that the various features of the drawings may not to-scale.

FIG. 1. Misoprostol is protective in the murine middle cerebral artery occlusion-reperfusion (MCAO-RP) model, in accordance with embodiments of the present invention. (A) Infarct volumes measured in cerebral cortex, caudate-putamen (CdPt), and hemisphere in mice treated with vehicle or misoprostol (1 mg/kg) and subjected to 90 min MCAO with 22.5 hour survival (n=10-11 per group; *p<0.05). (B) Representative coronal sections stained with triphenyltetrazolium chloride (TTC) at 24 hours showing preservation of tissue with misoprostol administration. (C) Misoprostol protected against ischemic infarction in cerebral cortex, CdPt, and hemisphere when given two hours after MCAO (n=10-11 per group; *p<0.05). (D) Cerebral blood flow (CBF) was measured using Laser Doppler flowmetry during ischemia and reperfusion and did not show differences between vehicle and misoprostol (n=4 per condition). LDF data was the average of values at 15 min intervals during ischemia/reperfusion. (E) Infarct volumes remained significantly reduced at 72 hours after MCAO (n=5 and 7 per group; *p<0.05) when misoprostol was given 2 hours after MCAO, and again at 6 h and 12 h after MCAO. Physiological parameters did not differ between vehicle and misoprostol treatments (see Table 1).

Figure 2:
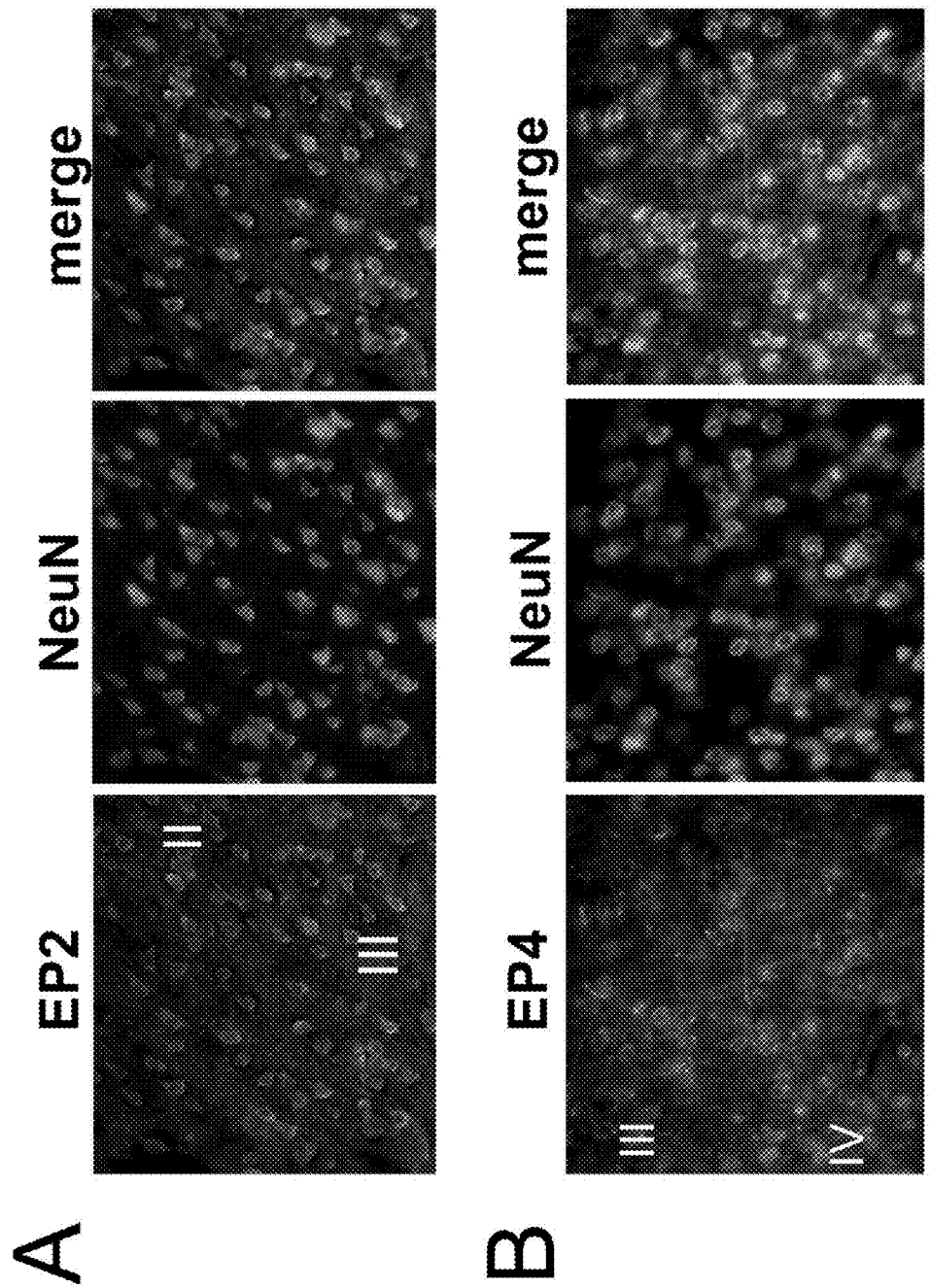

FIG. 2. EP2 and EP4 receptors are expressed in neurons under basal conditions (400× magnification), in accordance with embodiments of the present invention. Colocalization studies with the neuron-specific marker NeuN demonstrates staining of (A) EP2 and (B) EP4 in cortical neurons in frontal cortex. Both EP2 and EP4 were broadly expressed in neurons of cerebral cortex, striatum, and hippocampus.

Figure 3:
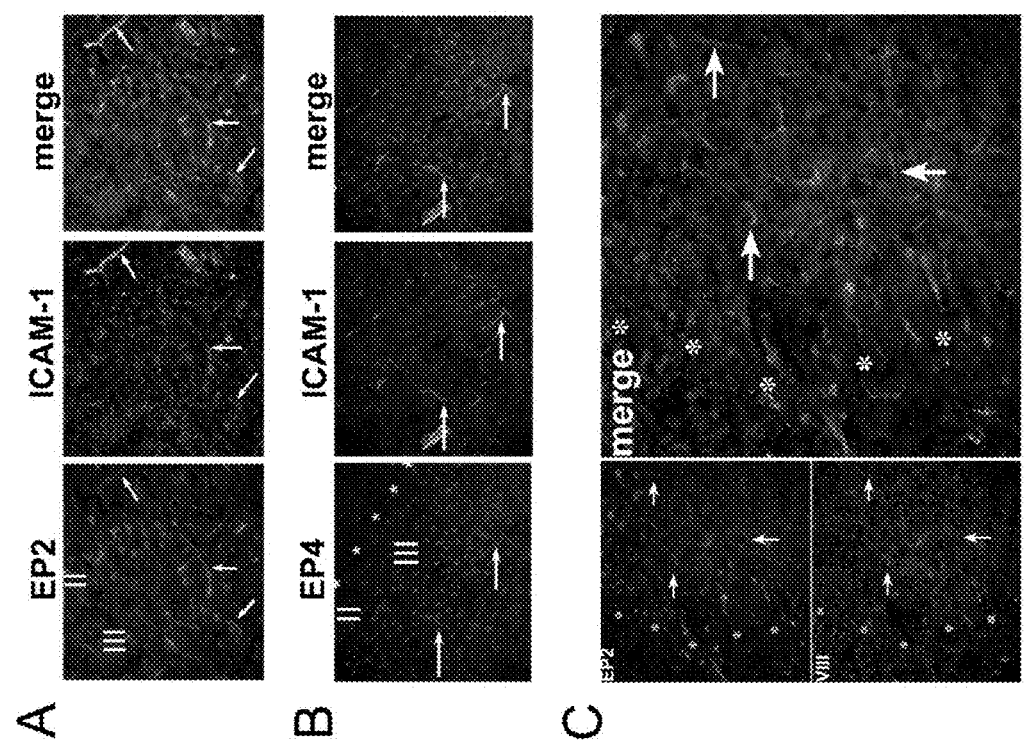

FIG. 3. EP2 and EP4 are dynamically regulated in neurons and endothelial cells during reperfusion after MCAO (200× magnification), in accordance with embodiments of the present invention. In frontal cortex, layers II and III, at 4 hours of reperfusion, EP2 (A) and EP4 (B) colocalize with the inter-cellular adhesion molecule 1 (ICAM-1) in endothelium (arrows) in the infarct and peri-infarct areas. (A) EP2 is expressed in microvessels and scattered neurons in the infarcted zone as well as the peri-infarct area (not shown). Note scattered clusters of EP2 stained neurons remaining in infarcted zone in layer II. (B) EP4 is expressed only in the peri-infarct zone at 4 hours of reperfusion in neurons and endothelium. Asterisks delineate the boundary between infarct zone (upper right corner) and the peri-infarct zone (lower left portion of image). (C) At 24 hours after MCAO, only EP2 expression persists in endothelium in the peri-infarct area (to the right of asterisks; arrows). There is scattered neuronal staining in the peri-infarct zone. For all sections, the boundaries between peri-infarct and infarcted zones were defined in adjacent sections with NeuN staining.

Figure 4:
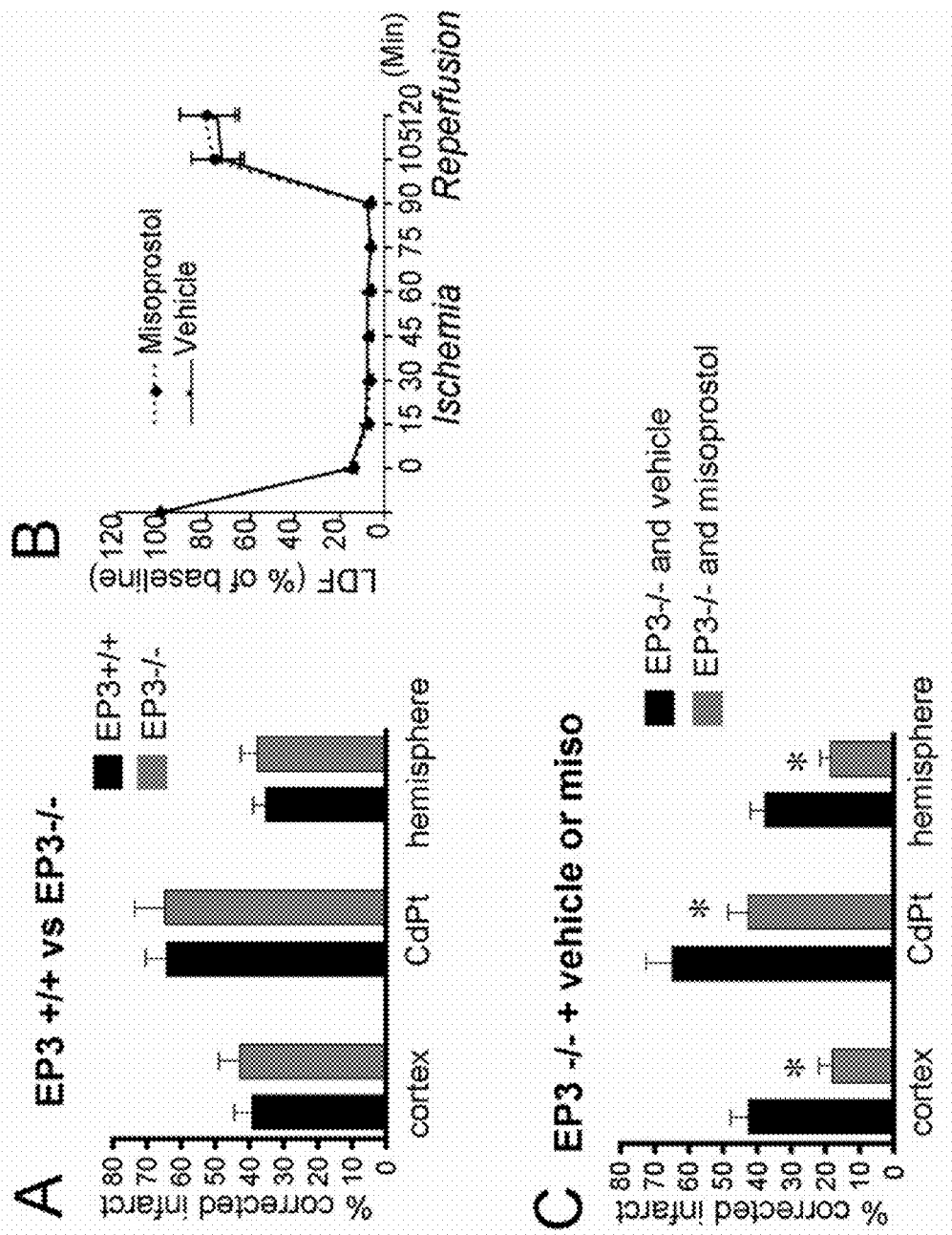

FIG. 4. The EP3 receptor does not transduce the protective effect of misoprostol in MCAO-RP, in accordance with embodiments of the present invention. (A) EP3−/− and +/+ mice do not show differences in infarct volumes at 24 hours (n=10 per genotype). (B) CBF as measured by Laser Doppler flowmetry during ischemia and reperfusion did not show differences between EP3+/+ and −/− mice (n=4 per condition). (C) Administration of misoprostol to EP3−/− mice results in similar reductions in infarct volume in EP3−/− and +/+ mice (n=10-11 per group; *p<0.05). Physiological measurements did not differ between genotypes (see Table 2).

Figure 5:
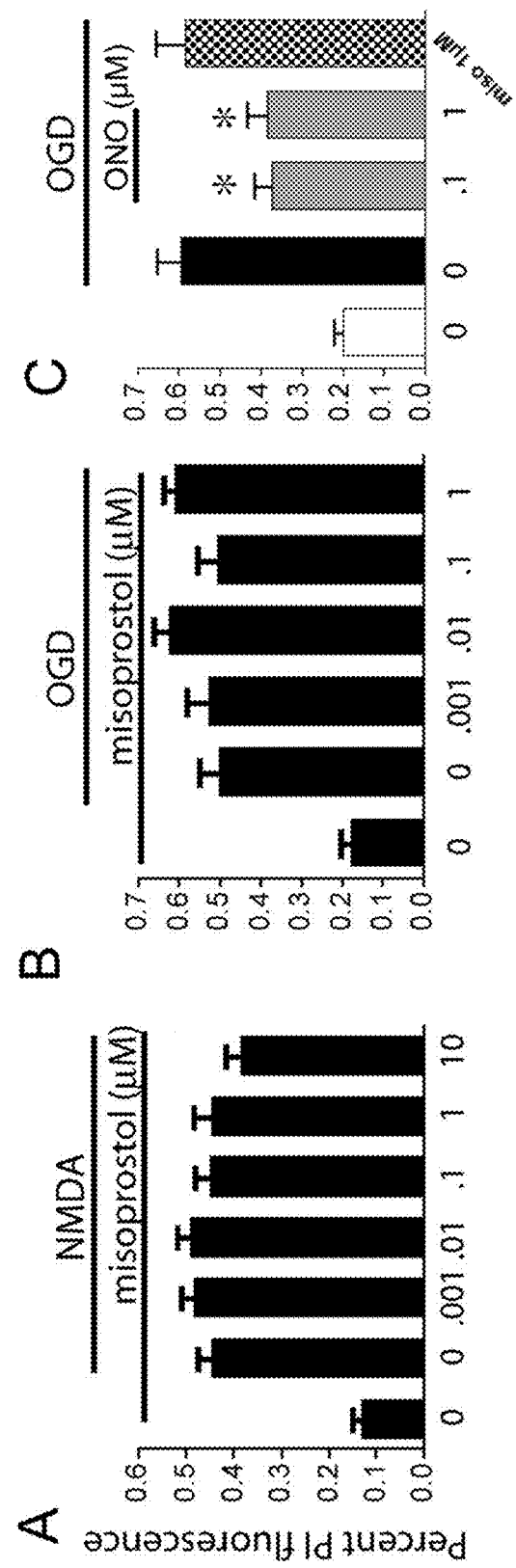

FIG. 5. Misoprostol does not protect hippocampal CA1 neurons against NMDA or OGD toxicity in organotypic cultures, in accordance with embodiments of the present invention. Hippocampal organotypic cultures were prepared and subjected to either oxygen glucose deprivation (OGD) or N-methyl D-aspartate (NMDA) in the presence or absence of misoprostol. Hippocampal organotypic slices were treated with NMDA (10 µM for 1 hour) (A) or subjected to OGD for 1 hour (B). Neuronal death was assayed by quantification of mean PI fluorescence in the CA1 subregion of each hippocampal slice. No differences were identified following misoprostol administration (n=15 slices per condition, experiments repeated 3 and 6 times for OGD and NMDA, respectively). Misoprostol also did not rescue primary cortical or hippocampal neurons stimulated with glutamate (50 µM; data not shown). (C) The $EP_4$ agonist ONO-AE1-329 rescues CA1 neurons in this model of OGD (p<0.02), but misoprostol does not.

Figure 6:
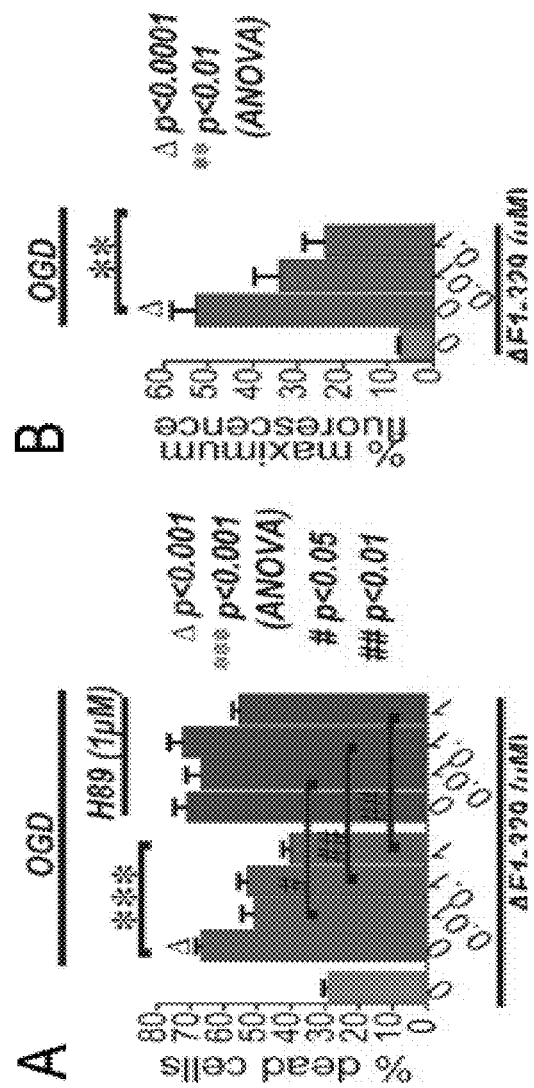

FIG. 6. Protective effect of EP4 activation in hippocampal neurons and organotypic slices subjected to OGD, in accordance with embodiments of the present invention. (A) ONO AE1-329 protects neurons from 3 h OGD in a dose-dependent manner (Δ control vs OGD; *dose response), but this can be reversed by inhibiting cAMP-dependent protein kinase A (PKA) with H89 (# and ## differences between AE1-329 and AE1-329+H89). (B) ONO AE1-329 also protects CA1 neurons in hippocampal slices subjected to OGD in a dose dependent manner (Δ control vs OGD; dose response. n=4-6 wells per condition for all experiments.

Figure 7:
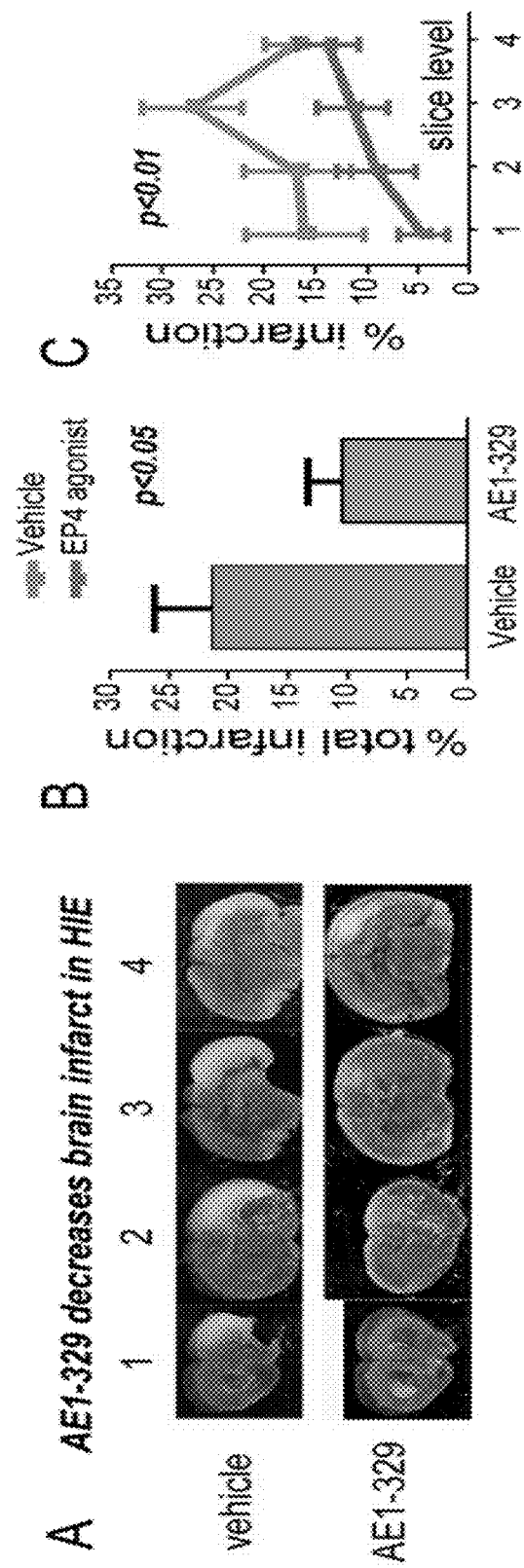

FIG. 7. ONO AE1-329 significantly decreases brain infarction in post natal rats subjected to hypoxic-ischemic encephalopathy (HIE), in accordance with embodiments of the present invention. (A) Representative TTC stained sections 24 hours after HIE. The HIE was carried out according to the established protocol of Sheldon (Sheldon et al., 1998), in which unilateral ligation of the left carotid artery is followed by 90 minute exposure to low oxygen (8% $O_2$/92% $N_2$) to induce a unilateral infarction of striatum and cortex. 24 hours following reoxygenation, brains sections were stained with TTC to assess infarct size. ONO AE1-329 administration (0.05 mg/kg SQ) after hypoxia significantly reduced infarct size at 24 hours. (B) Percent of hemispheric infarct volume was significantly reduced with administration of ONO AE1-329 (n=12-14 per treatment group; $p<0.05$). (C) The percent area of infarction was also reduced when measured by individual slice levels 1 through 4 (2-way ANOVA effect of treatment $F[1,24]=9.91$, $p<0.01$).

Figure 8:
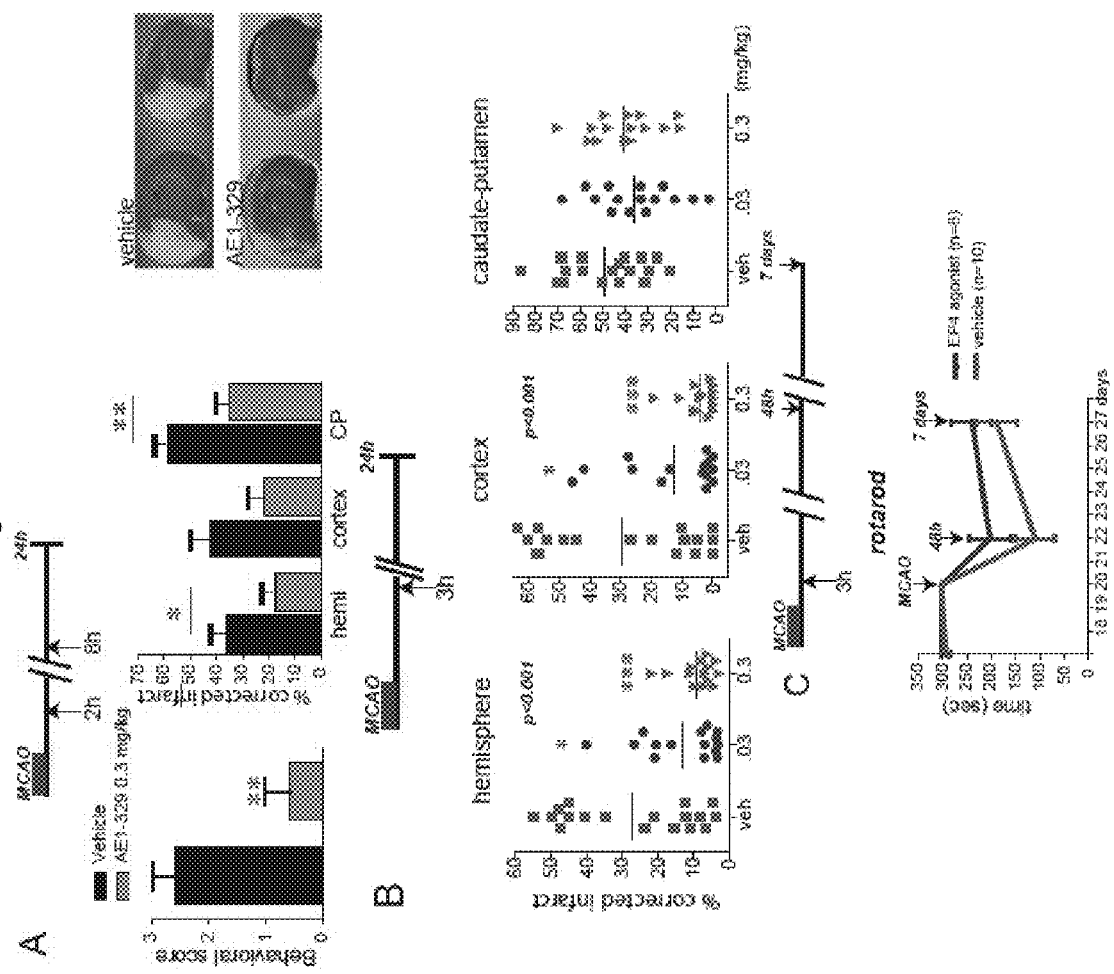
Figure 9:
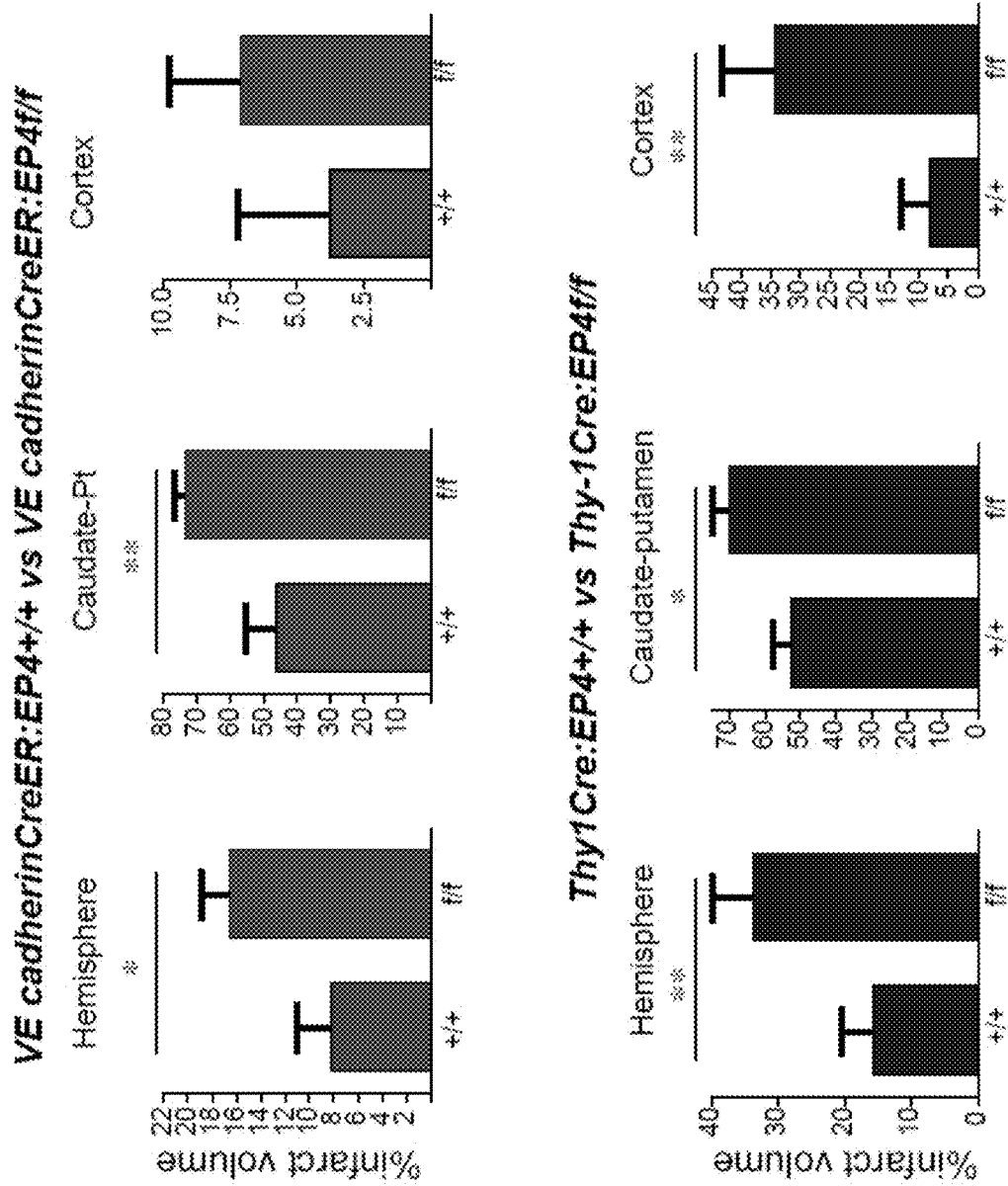

FIG. 8. Administration of $PGE_2$ $EP_4$ receptor agonist after cerebral ischemia is protective and rescues brain tissue, in accordance with embodiments of the present invention. (A) 3 months old male C57B6 mice underwent 60 min MCAO followed by reperfusion for 24 h. The administration of ONO-AE1-329 ('$EP_4$ agonist') at 0.3 mg/kg at 2 hours after MCAO and subsequently at 8 hours after MCAO resulted in significant rescue of infarcted tissue. (*$p<0.05$; $p<0.01$). This rescue of infarcted tissue is also demonstrated in the panel to the right which shows representative 2,3,5-Triphenyltetrazolium chloride (TTC) stained sections from vehicle (veh) in comparison to $EP_4$ agonist ONO AE1-329 (0.3 mg/kg) treated mice. The TTC stains of ONO AE1-329 treated mice show increased brain tissue viability and reduced infarct size compared to vehicle treated mice. Behavioral scores show significant rescue at 24 h after MCA occlusion in agonist-treated mice and significant reductions in infarct volume at 24 h after MCA occlusion. (B) The administration of ONO AE1-329 to male C57B6 mice at 0.03 and 0.3 mg/kg 3 hours after MCA occlusion resulted in a dose-dependent reduction in stroke infarct volume. There was a significant rescue of brain tissue with both doses ($p<0.01$, *$p<0.05$; 1-way ANOVA for hemisphere and cortex was $p<0.02$, and for caudate/putamen $p<0.01$ for n=6 veh, n=7 at 0.3 mg/kg, and n=6 at 0.03 mg/kg). (C) The administration of ONO AE1-329 at 0.03 mg/kg 3 hours after MCAO leads to improved rotarod performance at 48 hours and 7 days after infarction FIG. 9. Cell-specific deletion of endothelial $PGE_2$ $EP_4$ receptor or neuronal $PGE_2$ $EP_4$ receptor significantly increases infarct volume, in accordance with embodiments of the present invention. Top panel: VE cadherin Cre ER:EP4+/+ and VE cadherin Cre ER:EP4f/f male mice (C57B6 background, n=6-8 per group, age 5-6 mo) were generated and subjected to 30 minutes of MCAO and examined at 24 hours. Tamoxifen was administered to all mice at 8 weeks of age to induce Cre activation and excision of floxed $PGE_2$ $EP_4$ ($EP_4$) sequences. Conditional deletion of $EP_4$ in endothelial cells led to significant increases in infarct volume as compared to +/+$EP_4$ littermate controls (*$p<0.05$; **$p<0.01$). Bottom panel: Thy-1 Cre: $EP_4$f/f and Thy-1 Cre: $EP_4$+/+ female mice were generated and subjected to 60 minutes of MCAO and examined at 24 hours. Conditional deletion of neuronal $EP_4$ resulted in significant increases in infarct volume (*$p<0.05$; **$p<0.01$).

DEFINITIONS

The practice of the present invention may employ conventional techniques of chemistry, molecular biology, recombinant DNA, genetics, microbiology, cell biology, immunology and biochemistry, which are within the capabilities of a person of ordinary skill in the art. Such techniques are fully explained in the literature. For definitions, terms of art and standard methods known in the art, see, for example, Sambrook and Russell 'Molecular Cloning: A Laboratory Manual', Cold Spring Harbor Laboratory Press (2001); 'Current Protocols in Molecular Biology', John Wiley & Sons (2007); William Paul 'Fundamental Immunology', Lippincott Williams & Wilkins (1999); M. J. Gait 'Oligonucleotide Synthesis: A Practical Approach', Oxford University Press (1984); R. Ian Freshney "Culture of Animal Cells: A Manual of Basic Technique', Wiley-Liss (2000); 'Current Protocols in Microbiology', John Wiley & Sons (2007); 'Current Protocols in Cell Biology', John Wiley & Sons (2007); Wilson & Walker 'Principles and Techniques of Practical Biochemistry', Cambridge University Press (2000); Roe, Crabtree, & Kahn 'DNA Isolation and Sequencing: Essential Techniques', John Wiley & Sons (1996); D. Lilley & Dahlberg 'Methods of Enzymology: DNA Structure Part A: Synthesis and Physical Analysis of DNA Methods in Enzymology', Academic Press (1992); Harlow & Lane 'Using Antibodies: A Laboratory Manual: Portable Protocol No. I', Cold Spring Harbor Laboratory Press (1999); Harlow & Lane 'Antibodies: A Laboratory Manual', Cold Spring Harbor Laboratory Press (1988); Roskams & Rodgers 'Lab Ref: A Handbook of Recipes, Reagents, and Other Reference Tools for Use at the Bench', Cold Spring Harbor Laboratory Press (2002). Each of these general texts is herein incorporated by reference.

Unless defined otherwise, all technical and scientific terms used herein have the same meaning as commonly understood by a person of ordinary skill in the art to which this invention belongs. The following definitions are intended to also include their various grammatical forms, where applicable.

The terms "prostaglandin $E_2$ $EP_2$ and/or $EP_4$ receptor agonists", "$PGE_2$ $EP_2$ and/or $EP_4$ receptor agonists" and "$EP_2$ and/or $EP_4$ receptor agonists" are used interchangeably in this application.

The term "ischemic episode", as used herein, relates to any circumstance or condition that results in a deficient supply of blood to a tissue; as a consequence, this tissue becomes hypoxic due to a pursuant deficiency in oxygen supply (hypoxia). When the ischemia is associated with a stroke, it can be either global or focal ischemia, as defined below. The term "ischemic stroke" refers more specifically to a type of stroke that is of limited extent and caused due to blockage of blood flow. Cerebral ischemic episodes result from a deficiency in the blood supply to the brain. The spinal cord, which is also a part of the central nervous system, is equally susceptible to ischemia resulting from diminished blood flow.

The term "focal ischemia", as used herein in reference to the central nervous system, relates to the condition that results from the blockage of a single artery that supplies blood to the brain or spinal cord, resulting in damage to the cells in the territory supplied by that artery.

The term "global ischemia", as used herein in reference to the central nervous system, relates to the condition that results from a general diminution of blood flow to the entire brain, forebrain, or spinal cord, which causes the death of brain tissue in selectively vulnerable regions throughout these tissues. The pathology in each of these cases is quite different, as are the clinical correlates. Models of focal ischemia apply to patients with focal cerebral infarction, while models of global ischemia are analogous to cardiac arrest, and other causes of systemic hypotension.

The terms "cerebroprotection" and "cerebroprotective", as used herein, refer to the rescue of brain tissue and prevention of brain tissue death during cerebral (brain) ischemic conditions.

The therapeutic agents of the present invention and their analogs may be provided as metabolic precursors or pharmaceutically acceptable derivatives, by which is intended a modified agent that possesses the desired pharmacological activity of the parent compound and that can be administered with pharmaceutically acceptable carriers. "Pharmaceutically acceptable carriers" encompass those approved for use in animals and humans and include but are not limited to diluents as well as adjuvants such as water, oils, saline, dextrose solutions, glycerol solutions and excipients such as starch, glucose, lactose, sucrose, gelatin, malt, rice, flour, chalk, silica gel, sodium stearate, glycerol monostearate, talc, sodium chloride, powdered non-fat milk, propylene glycol and ethanol. Pharmaceutically acceptable carriers may also include emulsifying agents or pH buffering compounds.

The term "subject", as used herein, encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. The term does not denote a particular age or gender.

The term "neurological disorder", as used herein, is defined here and in the claims as a disorder in which loss of neurons occurs either in the peripheral nervous system or in the central nervous system. Examples of neurologic disorders include acute disorders including: stroke, traumatic brain injury, peripheral nerve damage, spinal cord injury, anoxia, and hypoxia. For example, neuronal death may be a consequence of the exposure to hypoxia or ischemia.

The term "stroke", as used herein, broadly refers to the development of neurological deficits associated with impaired blood flow to the brain regardless of cause. Potential causes include, but are not limited to, thrombosis, hemorrhage and embolism. Current methods for diagnosing stroke include symptom evaluation, medical history, chest X-ray, ECG (electrical heart activity), EEG (brain nerve cell activity), CAT scan to assess brain damage and MRI to obtain internal body visuals. Thrombus, embolus, and systemic hypotension are among the most common causes for cerebral ischemic episodes. Other injuries may be caused by hypertension, hypertensive cerebral vascular disease, rupture of an aneurysm, an angioma, blood dyscrasias, cardiac failure, cardic arrest, cardiogenic shock, septic shock, head trauma, spinal cord trauma, seizure, bleeding from a tumor, or other blood loss.

The term "cardiac arrest", as used herein, is one example of systemic hypotension which is a common cause for cerebral ischemic episodes.

The term "therapeutic effect", as used herein, refers to a consequence of treatment, the results of which are judged to be desirable and beneficial. A therapeutic effect may include, directly or indirectly, the reduction or elimination of an ischemic episode or neurological disorder resulting from the exposure of neurons to ischemic conditions in a subject. A therapeutic effect may also include, directly or indirectly, the reduction or elimination of the progression of an ischemic episode or neurological disorder resulting from the exposure of neurons to ischemic conditions in a subject. Finally, a therapeutic effect may also include, directly or indirectly, the prevention of a neurological disorder which, absent therapeutic intervention, would result from the exposure of neurons to ischemic conditions in a subject The term "therapeutically effective amount" of one or more substances or active agents is an amount that is sufficient to provide a therapeutic effect. However, dosage levels are based on a variety of factors, including the type of injury, the age, the weight, the gender, the medical condition of the patient, the severity of the condition, the route of administration, and the particular active agent employed. Thus, the dosage regimen may vary widely, but can be determined routinely by a physician using standard methods.

The term "therapeutic agent" or "active agent", as used herein, refers to a drug, molecule, nucleic acid, protein, composition or other substance that provides a therapeutic effect. The term "active", as used herein, refers to the ingredient, component or constituent of the compositions of the present invention responsible for the intended therapeutic effect.

The term "enteral route of administration", as used herein, refers to the administration of a therapeutic agent by mouth, gastric feeding tube or duodenal feeding tube.

The term "parenteral route of administration", as used herein, refers to the administration of a therapeutic agent into a vein (intravenously), into an artery (intraarterially), into a muscle (intramuscularly), into the cerebrum (intracerebrally), into the cerebral ventricles (intracerebroventricularly), into the heart (intracardiacally), under the skin (subcutaneously) or into the peritoneum (intraperitoneally).

The term "inhalational route of administration", as used herein, refers to the administration of a therapeutic agent via inhalation, e.g. intranasally.

The term "pharmaceutical composition" refers to a chemical or biological composition suitable for administration to a subject. Such compositions may be specifically formulated for enteral, parenteral or inhalational routes of administration.

DETAILED DESCRIPTION

Methods and compositions are provided for the treatment of ischemic episodes, including but not limited to focal or global ischemia of the brain and central nervous system, as caused by stroke or cardiac arrest. Furthermore, the present invention relates to methods and compositions for the treatment or prevention of a neurological disorder that results from the exposure to ischemic episodes, including but not limited to focal or global ischemia of the brain and central nervous system, as caused by stroke or cardiac arrest.

Aspects of the invention include the use of $PGE_2$ $EP_2$ and/or $EP_4$ agonists, alone or in combination with an anti-thrombotic agent such as tissue plasminogen activator, as therapeutic agents for the treatment of ischemic episodes or the prevention of neuronal injury following the exposure to ischemic episodes. The administration of the respective therapeutic agent(s) may be systemic or localized to the brain.

In certain embodiments of the invention, the therapeutic agent is misoprostol alone or misoprostol in combination with an anti-thrombotic agent such as tissue plasminogen activator.

In further embodiments of the invention, the therapeutic agent is the $PGE_2$ $EP_4$ receptor agonist ONO-AE1-329 alone or in combination with an anti-thrombotic agent such as tissue plasminogen activator.

The invention also provides methods for the identification of compounds that selectively activate the $PGE_2$ $EP_2$ and/or $EP_4$ receptor and that are determined to be efficacious and therapeutically useful in the treatment of ischemic episodes or in the prevention of neuronal injury.

Rodent In-Vivo Models as Good Predictors of Ischemic Episodes in Humans

Several experimental stroke models exist; these models are indispensable for understanding the pathophysiology of brain ischemia (cerebral ischemia) and to develop novel drugs and investigative methodology. Stroke can be modeled in animals, such as rodents (for a review, see Duverger and MacKenzie, 1988; Bederson et al., 1986), by occluding certain cerebral arteries that prevent blood from flowing into particular regions of the brain, then releasing the occlusion and permitting blood to flow back into that region of the brain (reperfusion). These focal ischemia models are in contrast to global ischemia models, where blood flow to the entire brain is blocked for a period of time prior to reperfusion. Certain regions of the brain are particularly sensitive to this type of ischemic insult. The precise region of the brain that is directly affected is dictated by the location of the blockage and duration of ischemia prior to reperfusion. One model for focal cerebral ischemia uses middle cerebral artery occlusion (MCAO) in rodents, which mimics the increase in plasma catecholamines, electrocardiographic changes, sympathetic nerve discharge, and myocytolysis seen in the human patient population.

In-Vitro Models to Simulate Ischemic Episodes

Maintaining cultured cells or hippocampal slices in vitro in iCSF during oxygen glucose deprivation (OGD) provides a realistic simulation of in vivo events, which include a selective and delayed cell death in the hippocampal CA1 region, assessed by propidium iodide uptake. Cell death is glutamate receptor dependent, as evidenced by the mitigation of damage by blockade of the N-methyl-D-aspartate and the α-Amino-3-hydroxy-5-methyl-4-isoxazolepropionic acid receptors.

Drug Screening Methods

Drug screening methods generally involve conducting various types of assays to identify agents that affect tissue damage that occurs during ischemia. Thus, a library of compounds can be screened for potential cerebroprotective compounds against oxygen-glucose deprivation (OGD) induced cell death in neuronal primary cultures. The library of compounds can be commercially available, can be proprietary, or can be custom synthesized. When neurons are deprived of chemical energy, glutamate floods out of the neurons in which it is stored and over activates receptors in nearby cells. This leads to the entry of deadly amounts of calcium and sodium into the cells and causing a delayed cell death after 24 hours in culture. These conditions mimic the ischemic stroke.

Determining the in vivo efficacy of candidate compounds is also of particular interest. Candidate compounds may be administered to an animal in a model for stroke, as explained above, by occluding certain cerebral arteries that prevent blood from flowing into particular regions of the brain, then releasing the occlusion and permitting blood to flow back into that region of the brain (reperfusion). One preferred model for focal cerebral ischemia uses middle cerebral artery occlusion (MCAO) in rodents, which mimics the increase in plasma catecholamines, electrocardiographic changes, sympathetic nerve discharge, and myocytolysis seen in the human patient population.

Disease Conditions: Ischemic Episodes and Neuronal Injuries

The brain requires glucose and oxygen to maintain neuronal metabolism and function. Hypoxia refers to inadequate delivery of oxygen to the brain, and ischemia results from insufficient cerebral blood flow. The abrupt presentation of acute ischemic stroke results from the abrupt interruption of blood flow to a part of the brain. Most commonly this is from embolic or thrombotic arterial vascular occlusion, which may be visualized angiographically if symptoms are severe enough to warrant acute angiography. Other vascular events that can result in stroke syndromes include lacunar strokes, arteritis, arterial dissections, and cortical venous occlusions. Intraparenchymal intracranial hemorrhage from a variety of causes including spontaneous or hypertensive hemorrhages, vascular malformations, or aneurysmal origin are frequently encountered clinically and figure prominently in the initial stroke differential diagnosis.

The consequences of cerebral ischemia depend on the degree and duration of reduced cerebral blood flow. Neurons can tolerate ischemia for 30-60 minutes, but perfusion must be reestablished before 3-6 hours of ischemia have elapsed. Neuronal injuries can be less severe and reversible if flow is restored within a few hours, providing a window of opportunity for intervention. If flow is not reestablished to the ischemic area, a series of metabolic processes ensue. The neurons become depleted of ATP and switch over to anaerobic glycolysis. Lactate accumulates and the intracellular pH decreases. Without an adequate supply of ATP, membrane ion pumps fail. There is an influx of sodium, water, and calcium into the cell. The excess calcium is detrimental to cell function and contributes to membrane lysis. Cessation of mitochondrial function signals neuronal death.

Methods to Treat Ischemic Episodes

The treatment of stroke includes preventive therapies using, for example, antihypertensive and antiplatelet drugs, which control and reduce blood pressure and, thus, reduce the likelihood of stroke. The development of thrombolytic drugs such as t-PA (tissue plasminogen activator) has provided a significant advance in the treatment of ischemic stroke victims, although to be effective it is necessary to begin treatment very early, within about three hours after the onset of symptoms. These drugs dissolve blood vessel clots which block blood flow to the brain and which are the cause of approximately 80% of strokes (Kent et al., 2001; Albers, 2001).

Most strokes present as a deficit or loss of function. The key to diagnosis is the abrupt onset of symptoms and risk factors for cerebrovascular disease. Confusional states, agitation, and delirium have all been reported as a consequence of focal neurologic injury; structures involving the limbic cortex of the temporal lobes and the orbitofrontal regions are commonly involved. Sensory complaints of either unusual sensations or loss of sensation are common in parietal and thalamic strokes. At times the sensory manifestation of a stroke may take on the characteristics of another clinical condition. Chest pain and limb pain that mimicked that of myocardial infarction can also be experienced.

In embodiments of the present invention, agonists of the $PGE_2$ $EP_2$ and/or $EP_4$ receptor ("therapeutic agents") are administered in vivo to a subject who (i) has suffered a neurologic disorder associated with hypoxia, ischemia and possibly neuronal injury, or who (ii) is at risk for a neurologic disorder associated with hypoxia, ischemia and possibly neuronal injury. These therapeutic agents can be administered up to 12 hours or longer after the onset of an ischemic episode and still be efficacious.

A therapeutically effective amount of the therapeutic agent(s) is delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the therapeutically effective amount for a given situation can be determined by routine experimentation. For purposes of the present invention, generally a therapeutically effective amount may be in the range of about 0.001 mg/kg to about 100 mg/kg body weight, in at least one dose. A therapeutically effective amount of the therapeutic agent(s) may be administered to the subject by an enteral, parenteral or inhalational route of administration in as many doses as is required to reduce and/or alleviate the signs, symptoms, or causes of the disorder in question, or bring about any other desired alteration of a biological system.

The therapeutic agents of the present invention can also be administered in conjunction with anti-thrombotic or thrombolytic agents such as tissue plasminogen activator and derivatives thereof, e.g. monteplase, TNK-rt-PA, reteplase, lanoteplase, alteplase, pamiteplase, streptokinase; urokinase; APSAC; r-Prourokinase; heparin; staphylokinase; and the like that are known to be useful to treat or ameliorate symptoms associated with neurological disorders or neuronal injuries. Any of these agents may be administered together (concurrently or sequentially within 24 hours) with a therapeutic agent, in accordance to embodiments of the present invention, to treat a subject following hypoxia/ischemia. The anti-thrombotic or thrombolytic agents may be administered together with therapeutic agents of the present invention and their pharmaceutical formulations ("pharmaceutical compositions") by an enteral, parenteral or inhalational route of administration.

The cerebroprotective activity of experimental, candidate compounds may be determined with in vitro and in vivo assays. For example, cell cultures are used in screening agents for their effect on neural cells and/or brain tissue and neurologic events, e.g. during ischemia.

The data obtained from cell culture and/or animal studies can be used in formulating a range of dosages for humans. The dosage of the active ingredient typically lies within a range of circulating concentrations that include the $ED_{50}$ with low toxicity. The dosage can vary within this range depending upon the dosage form employed and the route of administration utilized.

Misoprostol

Misoprostol is a widely used anti-ulcer agent in patients who are at risk for non-steroidal anti-inflammatory drug (NSAID)-mediated gastritis and ulcer disease (Numo, 1992) and repletes cytoprotective levels of $PGE_2$ necessary for maintaining integrity of the gastric mucosa. Misoprostol reportedly binds to the $PGE_2$ $EP_2$, $EP_3$ and $EP_4$ receptors (Breyer et al., 2001). While the $EP_2$ and $EP_4$ receptors couple positively to $G_S$ to increase the formation of the intracellular messenger cAMP, the $EP_3$ receptor couples negatively to $G_i$ to decrease cAMP formation (McCullough et al., 2004). Based on our recent data demonstrating a protective role of the EP2 receptor in cerebral ischemia (Liu et al., 2005; McCullough et al., 2004), we tested whether misoprostol would reduce infarct volume in the MCAO model of transient focal ischemia.

Subcutaneous injection of misoprostol resulted in significant reductions in infarct size when given at the time of MCAO and two hours after the onset of MCAO, with comparable protection at 24 h and 72 h after MCAO. There were no differences in blood flow as measured by LDF or physiological measurements between treatments.

The administration of 1 mg/kg of misoprostol at the onset of 90 minutes of MCAO, followed by subsequent injections at 6 and 12 hours of reperfusion resulted in a significant rescue of tissue at 24 hours (FIGS. 1A and B). Neurological scores were significantly improved in the misoprostol treated cohort (2.4+/−0.2 vs 1.8+/−0.2; $p<0.05$). A second cohort of mice was subjected to MCAO-RP, with misoprostol administered 2 hours after MCAO, and two subsequent doses at 8 hours and 14 hours. Here, post-MCAO administration of misoprostol again resulted in a significant rescue in cerebral cortex, striatum and hemisphere (FIG. 1C). Neurological scores were also significantly improved in the misoprostol treated group in this cohort (2.6+/−0.3 vs 1.7+/−0.3, $p<0.05$). Laser Doppler flow measurements did not demonstrate any differences in flow between vehicle and misoprostol groups (FIG. 1D). A final cohort received misoprostol 2 hours after MCAO and again at 6 h and 12 h, and brains were examined at 72 hours. Comparable protection was seen at this delayed time point (FIG. 1E). Neurological scores were also significantly improved with misoprostol treatment (2.6+/−0.24 vs 1.0+/−0.22 vs, $p<0.05$). These studies indicate that subcutaneous administration of misoprostol significantly reduced stroke volume and improved neurological scores if given at the time of MCAO or 2 hours after onset of MCAO out to 72 hours of reperfusion. We believe that misoprostol exerted this pronounced protective effect in vivo in the MCAO model followed by reperfusion through its activation of both the $PGE_2$ $EP_2$ and $EP_4$ receptors in vivo.

$PGE_2$ $EP_4$ Receptor Agonist ONO-AE1-329

ONO-AE1-329 is a potent and selective $PGE_2$ $EP_4$ receptor agonist discovered and developed by ONO Pharmaceuticals. Further details are described in Shibuya et al., 2002.

ONO-AE1-329 was found to mediate a dose dependent pro-survival effect in primary embryonic neurons and in organotypic hippocampal slices (see FIG. 6), as well as in cultured endothelial cells (not shown). This protection appeared to be dependent on intact PKA signaling, because neuronal $PGE_2$ $EP_4$ protection was abolished with addition of the PKA inhibitor H89. In addition, a significant cerebroprotective effect of $EP_4$ in vivo in acute stages of cerebral ischemia was observed in the MCAO-RP model (see FIG. 8) as well as in the HIE model (see FIG. 7).

Pharmacologic activation of the $EP_4$ receptor upon administration of ONO-AE1-329 resulted in a significant rescue of cerebral tissue in the middle cerebral artery occlusion-reperfusion (MCAO-RP) model when given 3 hours after MCAO. In vitro, $EP_4$ receptor activation rescued neurons from NMDA and oxygen glucose deprivation in a protein kinase A (PKA) dependent manner (see FIG. 8). In vivo in mice, conditional knockout of neuronal $EP_4$ receptors worsened stroke outcome, indicating a critical protective role of endogenous neuronal $EP_4$ signaling in cerebral ischemia. In addition, conditional knockout of $EP_4$ receptor in endothelial cells significantly worsened stroke outcome, indicating that endothelial $EP_4$ receptor activation also is protective in cerebral ischemia. Examination of relative cerebral blood flow revealed decreased reperfusion in VE-cadherin CreER:$EP_4$f/f mice, suggesting that $EP_4$ signaling in cerebral endothelium is important in reperfusion (see FIG. 10).

In-Vitro Mouse Models of the Acute Phase of Ischemia

To model the acute phase of stroke, and to test the function of the $PGE_2$ $EP_2$ as well as $EP_4$ receptors, we separately examined pro-survival effects of the $PGE_2$ $EP_2/EP_4$ agonist misoprostol as well as the pro-survival effects of the $PGE_2$ $EP_4$ agonist ONO-AE1-329 in vitro in cultured neurons, organotypic hippocampal slices, and cultured endothelial cells (see Experimental Procedures for details). In contrast to ONO-AE1-329 (see FIGS. 5, 6), no protective effect was observed with misoprostol in-vitro (FIG. 5).

In-Vivo Mouse Models of the Acute Phase of Ischemia

Two distinct animal models were used: the hypoxic-ischemic encephalopathy (HIE) model of peri-natal ischemia and the middle cerebral artery occlusion-reperfusion (MCAO-RP) model of transient focal ischemia in the adult (McCullough et al., 2004; Liu et al., 2005; Li et al., 2008).

Lack of Involvement of the $PGE_2$ $EP_3$ Receptor in Mediating the Observed Cerebroprotective Effects of Misoprostol in the MCAO-RP Model.

As mentioned earlier, Misoprostol reportedly binds to the $PGE_2$ $EP_2$, $EP_3$ and $EP_4$ receptors (Breyer et al., 2001). While the $PGE_2$ $EP_2$ and $EP_4$ receptors couple positively to $G_S$ to increase the formation of the intracellular messenger cAMP, the $PGE_2$ $EP_3$ receptor couples negatively to $G_i$ to decrease cAMP formation (McCullough et al., 2004). Investigating the roles of the $PGE_2$ $EP_2$, $EP_3$ and $EP_4$ receptors in the cerebroprotective function of misoprostol in the MCAO-RP model, the $PGE_2$ $EP_3$ receptor was found to not contribute to the cerebroprotective effect of misoprostol. As illustrated in FIG. 4A, $PGE_2$ $EP_3$-negative when compared with $PGE_2$ $EP_3$-positive mice did not show any differences in infarct volumes at 24 hours during ischemia and reperfusion (n=10 per genotype). As further illustrated in FIG. 4B, cerebral blood flow (CBF), as measured by Laser Doppler flowmetry, during ischemia and reperfusion did not show differences between $PGE_2$ $EP_3$-negative and $PGE_2$ $EP_3$-positive mice (n=4 per condition). As shown in FIG. 4C, the administration of misoprostol to $PGE_2$ $EP_3$-negative mice resulted in similar reductions in infarct volume in $PGE_2$ $EP_3$-negative mice when compared with $PGE_2$ $EP_3$-positive mice (n=10-11 per group; *p<0.05). Physiological measurements did not differ between genotypes (see Table 1).

TABLE 1

Physiological parameters measured in EP3+/+ and EP3−/− male mice prior to and 30 min after MCAO. Data are shown as mean ± SEM (n = 4). There were no significant differences noted.

|  | genotype | pH | $CO_2$ (mmHg) | $O_2$ (mmHg) | Glucose (mg/dl) | MABP (mmHg) |
|---|---|---|---|---|---|---|
| Pre-ischemia | WT | 7.38 ± 0.029 | 41.2 ± 4.2 | 115 ± 9.1 | 142 ± 12 | 70 ± 7.6 |
|  | EP3−/− | 7.38 ± 0.021 | 39.9 ± 3.2 | 113 ± 6.2 | 148 ± 20 | 69 ± 6.9 |
| Ischemia | WT | 7.32 ± 0.019 | 44.2 ± 3.6 | 105 ± 8.4 | 157 ± 28 | 72 ± 5.1 |
|  | EP3−/− | 7.31 ± 0.029 | 45.8 ± 3.4 | 101 ± 6.2 | 140 ± 25 | 72 ± 7.0 |

Similarities and Differences of the $PGE_2$ $EP_2$ and $EP_4$ Receptors.

As mentioned earlier, both the $PGE_2$ $EP_2$ and $EP_4$ receptors couple positively to $G_S$ to increase the formation of the intracellular messenger cAMP and are similar in this respect. While both receptors share a similar proximal carboxy terminal amino acid sequences, the $PGE_2$ $EP_4$ receptor carboxy terminus is significantly longer and contains additional amino acid sequences important in downstream signaling that are different from the $PGE_2$ $EP_2$ receptor. Consequently, due to the described differences in the $PGE_2$ $EP_2$ and $PGE_2$ $EP_4$ receptors, one cannot necessarily expect with certainty that the stimulation of the $PGE_2$ $EP_4$ receptor elicits a similar or identical effect as the stimulation of the $PGE_2$ $EP_2$ receptor does.

Expression of $PGE_2$ EP Receptors in Stroke

We have carried out immunocytochemistry colocalization studies of $PGE_2$ EP receptors during the course of transient focal ischemia with reperfusion. We have determined that the $PGE_2$ $EP_4$ receptor is dynamically regulated in forebrain during reperfusion selectively in neurons and endothelial cells in the acute phase (<24 h). We hypothesize that $PGE_2$ $EP_4$ functions in maintaining the integrity of the neurovascular unit early on during reperfusion.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are herein described.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, experimental procedures and examples will be described to illustrate parts of the invention.

EXPERIMENTAL PROCEDURES

The following methods and materials were used in the examples that are described further below.

Animals

The study was conducted in accordance with the National Institutes of Health guidelines for the use of experimental animals and protocols were approved by the Institutional Animal Care and Use Committee. For MCAO-RP studies, male mice aged 10-12 weeks (20-25 grams) were used. For the $PGE_2$ $EP_3$−/− and $PGE_2$ $EP_3$+/+MCAO-RP studies, male 12 week old mice were used.

Ischemic Model

Focal cerebral ischemia was induced by 90 minutes of reversible right middle cerebral artery occlusion (MCAO) under isofluorane anesthesia followed by 22.5 hours or 72 hours of reperfusion and terminal histopathology, as previously described (McCullough et al., 2004). Rectal temperature and intraischemic and 22.5-hour neurological deficits were assessed and did not show differences between genotypes or treatments. Monitoring of physiological variables and Laser Doppler Flowmetry (LDF) were performed in companion cohorts (n=4/group) (McCullough et al., 2004). No significant differences in the physiological variables of mice treated with vehicle in comparison to mice treated with misoprostol were observed (see Table 2).

TABLE 2

Physiological parameters measured in vehicle and misoprostol treated male mice 30 min after the start of MCAO. Data are shown as mean ± SEM (n = 4). There were no significant differences noted.

|  | pH | $CO_2$ (mmHg) | $O_2$ (mmHg) | Glucose (mg/dl) | MABP (mmHg) |
|---|---|---|---|---|---|
| Vehicle | 7.29 ± 0.031 | 49.3 ± 3.4 | 96.3 ± 15 | 138 ± 20 | 68 ± 3.8 |
| Misoprostol | 7.28 ± 0.029 | 54.3 ± 5.1 | 99 ± 7.7 | 124 ± 14 | 70 ± 3.3 |

Brain tissue was also harvested from sham and MCAO-RP mice for immunocytochemistry.

Generation of $PGE_2$ $EP_3$ Negative ($EP_3$−/−) Mice $PGE_2$ $EP_3$−/− mice were generated by crossing a conditional knockout $PGE_2$ $EP_3$ mouse line harboring loxP sites flanking exon 2 to C57BL/6 EIIa Cre mice. Mouse genomic clones containing the $PGE_2$ $EP_3$ gene locus were initially obtained by screening a 129S6/SvEvTAC library (Childrens Hospital Oakland Research Institute) with a rabbit $PGE_2$ $EP_3$ cDNA fragment derived from exons 1 and 2. A genomic fragment encompassing the $PGE_2$ $EP_3$ exon 2, from the middle of transmembrane domain VI to the C-terminal splice junction, and the contiguous gamma C-terminal coding region was isolated. This fragment was modified by replacement with a cDNA fragment from the beta splice variant so that the second exon was fused to the $EP_3$ beta C-terminus. This exon was flanked with loxP sites. The resulting plasmid was linearized with Not I and transfected into TL1 129SvEv ES cells. Correctly targeted cells were identified by Southern blot analysis and blastocyts were injected. Resultant $PGE_2$ $EP_3$ floxed mice were backcrossed 10 generations onto the C57BL/6 background. These animals were then crossed with C57BL/6 EIIa Cre mice to generate a global $PGE_2$ $EP_3$ deletion; resulting heterozygote progeny were selected for the absence of the EIIa Cre allele. Progeny were intercrossed to generate the homozygous $PGE_2$ $EP_3$-/- mice on a C57Bl/6 background.

In Vivo Treatment with Misoprostol

Mice were given 3 subcutaneous injections of either vehicle (hydroxypropyl-methyl cellulose; HPMC) or 1 mg/kg misoprostol in HPMC (1:100 misoprostol:HPMC; Pfizer, Groton, Conn.) (Best et al., 1995) either at onset of MCAO or 2 hours after MCAO, followed by two subsequent doses 6 and 12 hours later.

In the first experiment, misoprostol was given at onset of MCAO, with the two subsequent injections given at 6 hours and at 12 hours post MCAO, and brains were analyzed 22.5 hours later. In the second experiment, treatment with the initial dose of misoprostol was delayed two hours after the onset of MCAO, and two subsequent doses were then administered at 8 hours and 14 hours after MCAO and brains were analyzed at 22.5 hours later. In the third experiment, a delayed time point was tested, and misoprostol was given 2 hours after MCAO and again at 6 and 12 hours; brains were examined at 72 hours. A fourth experiment was carried out on a cohort of $PGE_2$ $EP_3$-/- and $PGE_2$ $EP_3$+/+ male mice (20-25 grams, 2-3 months old); these mice were subjected to MCAO and sacrificed at 22.5 hours. A fifth cohort of $EP_3$-/- and +/+ mice underwent treatment with either vehicle or misoprostol at MCAO, with subsequent administration of misoprostol or vehicle at 6 and 12 hours post MCAO and brain examination 22.5 hours later.

In Vivo Treatment with ONO-AE1-329

ONO-AE1-329 promoted significant rescue of brain tissue in the murine middle cerebral artery occlusion-reperfusion model of transient focal ischemia, when administered 2 and 8 hours after stroke onset. ONO-AE1-329 further promoted significant rescue of brain tissue in the murine middle cerebral artery occlusion-reperfusion model of transient focal ischemia, when administered only at 3 hours after stroke onset at doses of 0.3 mg/kg or 0.03 mg/kg.

Statistical Analysis

Statistical analysis was performed by Student's t-test or one-way analysis of variance (ANOVA), followed by Tukey post hoc analysis. All data are reported as mean±standard error of the mean (SEM). P values<0.05 were considered significant.

Terminal Histopathology

Mice were terminated at 22.5 hours or 72 hours after MCAO by decapitation and the intact brain was removed and cut into five 2 mm coronal sections, incubated in 1.5% 2,3,5-triphenyltetrazolium chloride (TTC), and analyzed (Inquiry, Loats Associates, Westminster, Md., USA) using SigmaScan Pro image analysis software. Infarct size was expressed as a percentage of the contralateral hemisphere/structure after correcting for edema, as previously described (McCullough et al., 2004).

Immunostaining

Brain tissue was harvested, processed, and immunostained as described previously (Kawano et al., 2006). Primary antibodies included anti-$PGE_2EP_2$, -$EP_3$, or -$EP_4$ receptor polyclonal antibodies (1:1000; Cayman Chemicals, Ann Arbor, Mich.), Neu N monoclonal antibody (1/1000; Chemicon, Temacula, Calif.), anti-ICAM-1 biotinylated antibody (1/1000; R&D Systems, Minneapolis, Minn.), anti-Iba I polyclonal antibody (1/500; Wako, Richmond, Va.), and anti-GFAP monoclonal antibody (1/2000; Dako, Carpenteria, Calif.). Secondary antibodies and detection reagents included donkey anti-mouse Alexa 555, anti-rabbit Alexa 486, Alexa-555 streptavidin, and Zenon 555 for detection of Iba1 (Molecular Probes, Eugene, Oreg.). Images were acquired with a Nikon E400 with an Orca ER CCD camera and digitized using Volocity software (Improvision). Negative controls consisted of omission of the primary antibody or use of blocking peptide, and in the case of $EP_2$, absence of specific signal in $EP_2$-/- brains.

Organotypic Hippocampal Slices

To assess in vitro effects of misoprostol as well as ONO-AE1-329 (see FIGS. 5 and 6), organotypic hippocampal cultures were prepared from post-natal day 7 pups and stimulated with oxygen glucose deprivation (OGD) or N-methyl D-aspartate (NMDA) as previously described (McCullough et al., 2004). Briefly, at 13 days in culture, fresh medium containing propidium iodide (PI; 5 µg/ml) was added to organotypic hippocampal slices, and basal PI fluorescence was measured the following day (time point $t_b$) as an indicator of basal cell death. Slices were then stimulated with 10 µM NMDA for 1 hour, or subjected to OGD for 1 hour, +/- misoprostol, vehicle, or the $PGE_2$ $EP_4$ agonist ONO-AE1-329; after stimulation, media was replaced with fresh media containing either agonist or vehicle and PI (5 µg/ml) for 23 hours. Slices were imaged 24 hours later ($t_{24h}$). Medium was then replaced with fresh medium containing a lethal dose of 10 µM NMDA and PI and incubated overnight to induce maximum CA1 neuronal loss and imaged 24 hours later ($t_{max}$). Neuronal death was assayed by quantification of mean PI fluorescence in the CA1 subregion of each hippocampal slice for $t_b$, $t_{24h}$, and $t_{max}$. The percent neuronal death was normalized for each individual slice and was calculated as follows: $(t_{24h}-t_b)/(t_{max}-t_b)$. Experiments were repeated 3-6 times, with n=15 slices per condition).

EXAMPLES

The following examples are put forth so as to provide those of ordinary skill in the art with a complete disclosure and description of how to make and use the present invention; they are not intended to limit the scope of what the inventors regard as their invention. Unless indicated otherwise, part are parts by weight, molecular weight is average molecular weight, temperature is in degrees Centigrade, and pressure is at or near atmospheric.

Example 1

Misoprostol Promotes Significant Rescue of Brain Tissue in the Murine Middle Cerebral Artery Occlusion-Reperfusion Model of Transient Focal Ischemia, when Administered At the Time of Stroke Onset as Well as 6 and 12 Hours Later Mice were given two subcutaneous injections of either vehicle (hydroxypropyl-methyl cellulose; HPMC) or 1 mg/kg misoprostol in HPMC (1:100 misoprostol:HPMC; Pfizer, Groton, Conn.) (Best et al., 1995) at onset of MCAO, followed by two subsequent doses 6 and 12 hours later. Brains were analyzed 22.5 hours later and, in a separate cohort, 72 hours later.

Example 2

Misoprostol Promotes Significant Rescue of Brain Tissue in the Murine Middle Cerebral Artery Occlusion-Reperfusion Model of Transient Focal Ischemia, when Administered 2 Hours after Stroke Onset as Well as 8, 14 and 72 Hours Later Mice were given two subcutaneous injections of either vehicle (hydroxypropyl-methyl cellulose; HPMC) or 1 mg/kg misoprostol in HPMC (1:100 misoprostol:HPMC; Pfizer, Groton, Conn.) (Best et al., 1995) 2 hours after MCAO, followed by two subsequent doses 8 and 14 hours later. Brains were analyzed 22.5 hours later.

Example 3

Immunolocalization of the Prostaglandin $EP_2$ and $EP_4$ Receptors in MCAO-RP To determine the cellular substrates of misoprostol signaling and protection, the temporal dynamics of PGE2 EP2, EP3, and EP4 receptor expression were investigated in sham and MCAO-RP mice at 4 hour and 24 hour after MCAO. Immunostaining for PGE2 EP3 was in accord with previous in situ hybridization studies (Ek et al., 2000) and showed no significant expression in striatum and cerebral cortex in sham and ischemic brains (data not shown). In sham treated mice, PGE2 EP2 and EP4 receptors co-localized with NeuN in neurons (FIGS. 2A and B; layers II-IV of frontal cortex), and also colocalized with Factor VIII, a marker of endothelial cells (not shown) indicating that the PGE2 EP2 and EP4 receptors are basally expressed in neurons and in endothelial cells. At 4 hours of reperfusion, neuronal PGE2 EP2 staining decreased in parallel with Neu N in neurons in the ischemic core, but EP2 expression persisted in peri-infarct NeuN positive neurons (data not shown). In addition, at 4 hours of reperfusion, PGE2 EP2 expression was markedly induced in endothelium in the peri-infarct area and ischemic zones (FIG. 3A), colocalizing with ICAM-1, which is induced in endothelial cells as well as microglia following MCAO-RP. EP4 showed a similar downregulation in neurons at 4 hours of reperfusion and a marked induction in endothelial cells (FIG. 3B).

At 24 hours after MCAO, PGE2 EP2 but not PGE2 EP4 receptor expression persisted in endothelium in the peri-infarct zone (FIG. 3C). Colocalization studies with GFAP and Iba1, markers of astrocytes and microglia, respectively, did not demonstrate localization of the PGE2 EP2 or EP4 receptors in these cell types during reperfusion (not shown). These data indicate that PGE2 EP2 and EP4 are dynamically regulated selectively in neurons and endothelium during the course of reperfusion. Neuronal expression of PGE2 EP2 and EP4 is lost in the ischemic core by 4 hours of reperfusion, but remains in the peri-infarct zone. In endothelium, levels of PGE2 EP2 and EP4 receptor expression are upregulated early in reperfusion at 4 hours in the ischemic core and peri-infarct areas; by 24 hours of reperfusion, vascular expression of PGE2 EP4 had disappeared, but PGE2 EP2 expression remained. The temporal dynamics of PGE2 EP2 and EP4 cellular expression suggest that the pharmacological protection by misoprostol may be mediated by neurons and/or endothelial cells.

Example 4

Testing Whether Misoprostol Exerts Protection Via the $EP_3$ Receptor

To further establish whether misoprostol is acting selectively via the PGE2 EP2 and/or EP4 receptors, we tested whether the PGE2 EP3 receptor mediated any protective effect by misoprostol. From previous studies, it has been demonstrated that the PGE2 EP2 receptor confers significant protection in the MCAO-RP model (Liu et al., 2005, McCullough et al., 2004) and that pharmacological activation of PGE2 EP4 protects in a striatal model of excitotoxicity (Ahmad et al., 2005). We first determined whether the PGE2 EP3 receptor functioned in MCAO-RP. C57B6 male PGE2 EP3−/− and +/+ mice were subjected to MCAO-RP.

In one a cohort of PGE2 EP3−/− and PGE2 EP3+/+ male mice (20-25 grams, 2-3 months old), mice were subjected to MCAO and sacrificed at 22.5 hours. Another cohort of PGE2 EP3−/− and +/+ mice underwent treatment with either vehicle or misoprostol at MCAO, with subsequent administration of misoprostol or vehicle at 6 and 12 hours post MCAO and brain examination 22.5 hours later.

Interestingly, infarct size and neurological scores did not show differences between genotypes (FIG. 4A; neurological scores for PGE2 EP3+/+: 2.5+/−0.3 versus PGE2 EP3−/− 2.0+/−0.2), indicating that the PGE2 EP3 receptor did not influence infarct size in vivo at the 24-hour time point. Moreover, administration of misoprostol to PGE2 EP3−/− mice did not diminish the protective effect of misoprostol, and resulted in similar decreases in infarct volume compared to PGE2 EP3+/+ mice given misoprostol. These findings indicate that the PGE2 EP3 receptor does not influence outcome in MCAO, and does not transduce the protective effect of misoprostol (FIG. 4B). Thus, these data, in combination with the immunostaining demonstrating a dynamic regulation of PGE2 EP2 and EP4 in penumbra with reperfusion suggest that the positive effects of misoprostol are likely mediated via the PGE2 EP2 and/or the EP4 receptors.

Example 5

ONO-AE1-329, but not Misoprostol, Protects Hippocampal CA1 Neurons Against NMDA or OGD Toxicity in Organotypic Cultures To assess in vitro effects of misoprostol as well as ONO-AE1-329 (see FIGS. 5 and 6), organotypic hippocampal cultures were prepared from post-natal day 7 pups and stimulated with oxygen glucose deprivation (OGD) or N-methyl D-aspartate (NMDA) as previously described (McCullough et al., 2004). Briefly, at 13 days in culture, fresh medium containing propidium iodide (PI; 5 μg/ml) was added to organotypic hippocampal slices, and basal PI fluorescence was measured the following day (time point tb) as an indicator of basal cell death. Slices were then stimulated with 10 μM NMDA for 1 hour, or subjected to OGD for 1 hour, +/− misoprostol, vehicle, or the PGE2 EP4 agonist ONO-AE1-329; after stimulation, media was replaced with fresh media containing either agonist or vehicle and PI (5 μg/ml) for 23 hours. Slices were imaged 24 hours later (t24 h). Medium was then replaced with fresh medium containing a lethal dose of 10 μM NMDA and PI and incubated overnight to induce maximum CA1 neuronal loss and imaged 24 hours later (tmax). Neuronal death was assayed by quantification of mean PI fluorescence in the CA1 subregion of each hippocampal slice for tb, t24 h, and tmax. The percent neuronal death was normalized for each individual slice and was calculated as follows: (t24 h−tb)/(tmax−tb). Experiments were repeated 3-6 times, with n=15 slices per condition).

While ONO-AE1-329 clearly protected hippocampal CA1 neurons against NMDA or OGD toxicity in organotypic cultures (FIGS. 5 and 6), misoprostol did not—in an apparent contrast to in-vivo studies. We trust the in-vivo results, since in-vivo studies generally provide more conclusive results and there are many reasons that in-vitro studies, since they represent an isolated system, do not always minor in-vivo results.

Example 6

ONO-AE1-329 Promotes Significant Rescue of Brain Tissue in the Murine Middle Cerebral Artery Occlusion-Reperfusion Model of Transient Focal Ischemia, when Administered 2 and 8 Hours after Stroke Onset 3 months old male C57B6 mice underwent 60 min MCAO followed by reperfusion for 24 h. As illustrated in FIG. 8A, the administration of ONO-AE1-329 ('EP4 agonist') at 0.3 mg/kg at 2 hours after MCAO and subsequently at 8 hours at 0.3 mg/kg after MCAO resulted in significant rescue of infarcted tissue. (*$p<0.05$; **$p<0.01$) and reduction in behavioral deficits at 24 hours (n=12 vehicle and n=7 PGE2 EP4 agonist treated mice).

Example 7

ONO-AE1-329 Promotes Significant Rescue of Brain Tissue in the Murine Middle Cerebral Artery Occlusion-Reperfusion Model of Transient Focal Ischemia, when Administered Only at 3 Hours after Stroke Onset at Doses of 0.3 mg/kg or 0.03 mg/kg In another series of experiments, the PGE2 EP4 agonist ONO-AE1-329 was administered only once at 3 h after MCAO at 0.3 mg/kg or 0.03 mg/kg (FIG. 8B). There was a significant rescue of brain tissue with both doses (**$p<0.01$, *$p<0.05$; 1 way ANOVA for hemisphere and cortex was $p<0.02$, and for caudate/putamen $p<0.01$). This indicates that administration of PGE2 EP4 agonist at 3 hours after MCAO results in significant rescue of brain tissue at 24 hours (n=6 veh, n=7 at 0.3 mg/kg, and n=6 at 0.03 mg/kg).

Example 8

Prostaglandin $E_2$ EP4 Receptor is Cerebroprotective in Stroke Via Neuronal and Endothelial Cell Signaling Prostaglandin E2 (PGE2) is a lipid messenger derived from the metabolism of arachidonic acid by the cyclooxygenases COX-1 and COX-2. PGE2 signals through a class of four distinct G-protein coupled receptors, the EP1-4 receptors. Levels of PGE2 are markedly induced in experimental stroke and contribute to COX-2 mediated cerebral injury via EP1 receptor signaling. However, recent epidemiologic studies indicate that chronic COX-2 inhibition results in adverse cerebrovascular and cardiovascular effects, indicating that certain downstream prostaglandin signaling pathways may in fact be beneficial.

We investigated the function of the PGE2 EP4 receptor, which is expressed in forebrain in neurons and is markedly induced in endothelial cells after transient focal cerebral ischemia. Pharmacologic activation of the EP4 receptor resulted in a significant rescue of cerebral tissue in the middle cerebral artery occlusion-reperfusion (MCAO-RP) model when given 3 hours after MCAO. In vitro, EP4 receptor activation rescued neurons from NMDA and oxygen glucose deprivation in a protein kinase A (PKA) dependent manner (see FIG. 8). In vivo, conditional knockout of neuronal EP4 receptors worsened stroke outcome, indicating a critical protective role of endogenous neuronal EP4 signaling in cerebral ischemia. In addition, conditional knockout of EP4 receptor in endothelial cells significantly worsened stroke outcome, indicating that endothelial EP4 receptor activation also is protective in cerebral ischemia. Examination of relative cerebral blood flow revealed decreased reperfusion in VE-cadherin CreER: EP4f/f mice, suggesting that EP4 signaling in cerebral endothelium is important in reperfusion. These findings demonstrate the existence of cell-specific EP4 receptor signaling pathways that mediate cerebroprotection of EP4 in cerebral ischemia. The endothelial and neuronal EP4 receptors represent novel therapeutic targets in stroke.

Although the foregoing invention and its embodiments have been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention. It will be appreciated that those skilled in the art will be able to devise various arrangements which, although not explicitly described or shown herein, embody the principles of the invention and are included within its spirit and scope.

REFERENCES

Ahmad A S, Ahmad M, de Brum-Fernandes A J, Dore S. "Prostaglandin EP4 receptor agonist protects against acute neurotoxicity". *Brain Res* 1066 (2005), pp. 71-77.
Albers G W: Advances in intravenous thrombolytic therapy for treatment of acute stroke. *Neurology* 57 (2001)(5 Suppl 2): pp. S77-81.
Bederson J B, Pitts L H, Tsuji M, Nishimura M C, Davis R L and Bartkowski H. Rat middle cerebral artery occlusion: evaluation of the model and development of a neurologic examination. *Stroke* 17 (1986), pp. 472-476.
Best V, Ruiz P, Spurney R F. The Prostaglandin E(1) (PGE(1)) Analog Misoprostol Ameliorates Autoimmune Disease and Depletes T Lymphocytes in MRL-lpr/lpr Mice. *Am J Ther* 2 (1995), pp. 943-948.
Breyer R M, Bagdassarian C K, Myers S A, Breyer M D. Prostanoid receptors: subtypes and signaling. *Annu Rev Pharmacol Toxicol* 41 (2001), pp. 661-690.
Coleman R A, Smith W L and Narumiya S. International Union of Pharmacology classification of prostanoid receptors: properties, distribution, and structure of the receptors and their subtypes. *Pharmacol Rev* 46 (1994), pp. 205-229.
Donnan G A, Fisher M, Macleod M, Davis S M. "Stroke". *Lancet* 371 (2008): pp. 1612-23.
Dore S, Otsuka T, Mito T, Sugo N, Hand T, Wu L, Hurn P D, Traystman R J, Andreasson K. Neuronal overexpression of cyclooxygenase-2 increases cerebral infarction. *Ann Neurol* 54 (2003), pp. 155-162.
Duverger D and MacKenzie E T. The quantification of cerebral infarction following focal ischemia in the rat: influence of strain, arterial pressure, blood glucose concentration, and age. *J Cereb Blood Flow Metab* 8 (1988), pp. 449-461.

Ek M, Arias C, Sawchenko P, Ericsson-Dahlstrand A. Distribution of the EP3 prostaglandin E(2) receptor subtype in the rat brain: relationship to sites of interleukin-1-induced cellular responsiveness. *J Comp Neurol* 428 (2000), pp. 5-20.

Iadecola C, Niwa K, Nogawa S, Zhao X, Nagayama M, Araki E, Morham S, Ross M E. Reduced susceptibility to ischemic brain injury and N-methyl-D-aspartate-mediated neurotoxicity in cyclooxygenase-2-deficient mice. *Proc Natl Acad Sci USA* 98 (2001), pp. 1294-1299.

Kawano T, Anrather J, Zhou P, Park L, Wang G, Frys K A, Kunz A, Cho S, Orio M, Iadecola C. Prostaglandin E2 EP1 receptors: downstream effectors of COX-2 neurotoxicity. *Nature Medicine* 12 (2006), pp. 225-229.

Kent T A, Soukup V M, Fabian R H. Heterogeneity affecting outcome from acute stroke therapy: making reperfusion worse. *Stroke* 32 (2001), pp. 2318-27.

Li J, Liang X, Wang Q, Breyer R M, McCullough L, Andreasson K. Misoprostol, an antiulcer agent and PGE(2) receptor agonist, protects against cerebral ischemia. *Neurosci Lett* 438 (2008), pp. 210-215.

Liu D, Wu L, Breyer R, Mattson M P, Andreasson K. Neuroprotection by the PGE2 EP2 receptor in permanent focal cerebral ischemia. *Ann Neurol* 57 (2005), pp. 758-761.

McCullough L, Wu L, Haughey N, Liang X, Hand T, Wang Q, Breyer R M, Andreasson K. Neuroprotective function of the PGE2 EP2 receptor in cerebral ischemia. *J Neurosci* 24 (2004), pp. 257-268.

Nagayama M, Niwa K, Nagayama T, Ross M E, Iadecola C. The cyclooxygenase-2 inhibitor NS-398 ameliorates ischemic brain injury in wild-type mice but not in mice with deletion of the inducible nitric oxide synthase gene. *J Cereb Blood Flow Metab* 19 (1999), pp. 1213-1219.

Narumiya S, Sugimoto Y, Ushikubi F. Prostanoid Receptors: Structures, Properties, and Functions. *Physiol. Rev.* 79 (1999), pp. 1193-1226.

Nogawa S, Forster C, Zhang F, Nagayama M, Ross M E, Iadecola C. Interaction between inducible nitric oxide synthase and cyclooxygenase-2 after cerebral ischemia. *Proc Natl Acad Sci USA* 95 (1998), pp. 10966-10971.

Numo R. Prevention of NSAID-induced ulcers by the coadministration of misoprostol: implications in clinical practice. *Scand J Rheum* 92 (1992), pp. 25-29.

Sheldon R A, Sedik C, Ferriero D M. Strain-related brain injury in neonatal mice subjected to hypoxia-ischemia. *Brain Res* 810 (1998), pp. 114-122.

Shibuya I, Setiadji S V, Ibrahim N, Harayama N, Maruyama T, Ueta Y, Yamashita H. Involvement of postsynaptic EP4 and presynaptic EP3 receptors in actions of prostaglandin E2 in rat supraoptic neurons. *J Neuroendrocrin* 14 (2002), pp. 64-72.

Smith, W L and Langenbach R. Why there are two cyclooxygenase isozymes *J. Clin. Invest.* 107 (2001), pp. 1491-1495.

White B C, Sullivan J M, DeGracia D J, O'Neil B J, Neumar R W, Grossman L I, Rafols J A, Krause G S. Brain ischemia and reperfusion: molecular mechanisms of neuronal injury. *J Neurol Sci* 179 (S1-2) (2000), pp. 1-33.

What is claimed is:

1. A method of treating an ischemic episode in a subject, the method comprising administering to said subject a composition comprising misoprostol and a pharmaceutically acceptable carrier, said composition administered in doses effective to achieve reduction in infarct volume of said subject's brain tissue.

2. A method of treating an ischemic episode in a subject, the method comprising administering to said subject within 24 hours after the onset of said ischemic episode the composition according to claim 1, furthermore comprising an anti-thrombotic agent, said composition administered in doses effective to achieve reduction in infarct volume of said subject's brain tissue.

3. A method of treating an ischemic episode in a subject, the method comprising administering to said subject within 24 hours after the onset of said ischemic episode the composition according to claim 2, wherein the anti-thrombotic agent is tissue plasminogen activator, said composition administered in doses effective to achieve reduction in infarct volume of said subject's brain tissue.

4. The method according to claim 1, wherein the ischemic episode is caused by a stroke.

5. The method according to claim 2, wherein the ischemic episode is caused by a stroke.

6. The method according to claim 3, wherein the ischemic episode is caused by a stroke.

7. The method according to claim 1, wherein the ischemic episode is caused by cardiac arrest.

8. The method according to claim 2, wherein the ischemic episode is caused by cardiac arrest.

9. The method according to claim 3, wherein the ischemic episode is caused by cardiac arrest.

\* \* \* \* \*